(12) United States Patent
Krauskopf et al.

(10) Patent No.: US 9,770,468 B2
(45) Date of Patent: Sep. 26, 2017

(54) USE OF WHEY PERMEATE FOR THE TREATMENT OF METABOLIC SYNDROME

(71) Applicant: "S.U.K." BETEILIGUNGS GMBH, Vienna (AT)

(72) Inventors: Jobst Krauskopf, Barum (DE); Christian Sowada, Norderstedt (DE)

( * ) Notice: Subject to any disclaimer, the term of this patent is extended or adjusted under 35 U.S.C. 154(b) by 265 days.

(21) Appl. No.: 13/930,693

(22) Filed: Jun. 28, 2013

(65) Prior Publication Data

US 2014/0017282 A1   Jan. 16, 2014

Related U.S. Application Data

(63) Continuation of application No. 10/564,075, filed as application No. PCT/EP2004/007690 on Jul. 12, 2004, now abandoned.

(30) Foreign Application Priority Data

Jul. 10, 2003 (DE) .................................. 103 31 202

(51) Int. Cl.
| | | |
|---|---|---|
| A61K 35/20 | (2006.01) | |
| A61K 31/19 | (2006.01) | |
| A61K 31/7016 | (2006.01) | |
| A23L 33/18 | (2016.01) | |
| A23L 33/19 | (2016.01) | |

(52) U.S. Cl.
CPC .............. *A61K 35/20* (2013.01); *A23L 33/18* (2016.08); *A23L 33/19* (2016.08); *A61K 31/19* (2013.01); *A61K 31/7016* (2013.01)

(58) Field of Classification Search
CPC ................................. A23C 21/06; A61K 35/20
See application file for complete search history.

(56) References Cited

U.S. PATENT DOCUMENTS

| | | | |
|---|---|---|---|
| 5,186,971 A * | 2/1993 | Girsh .................... | A23C 9/1422 426/491 |
| 5,213,826 A * | 5/1993 | Miller et al. ....................... | 426/2 |
| 5,639,501 A | 6/1997 | Vembu et al. | |
| 5,654,019 A | 8/1997 | Kobayashi et al. | |
| 6,096,870 A | 8/2000 | Mozaffar et al. | |
| 6,288,222 B1 * | 9/2001 | Roth et al. ..................... | 536/127 |
| 6,399,140 B1 | 6/2002 | Allen et al. | |
| 6,465,432 B1 | 10/2002 | Han et al. | |
| 6,919,314 B1 | 7/2005 | Schlothauer et al. | |
| 7,148,034 B2 | 12/2006 | Schlothauer et al. | |
| 8,106,152 B2 | 1/2012 | Reynolds et al. | |
| 2001/0022986 A1 * | 9/2001 | Girsh .................... | A23C 9/1425 426/583 |
| 2002/0025361 A1 * | 2/2002 | Kawachi et al. ............... | 426/74 |
| 2003/0004095 A1 * | 1/2003 | Reimer et al. .................... | 514/2 |
| 2003/0040461 A1 | 2/2003 | McAtee | |
| 2003/0118662 A1 | 6/2003 | Bastian et al. | |
| 2003/0166866 A1 | 9/2003 | Brody | |
| 2003/0195150 A1 | 10/2003 | Reynolds et al. | |
| 2003/0202992 A1 | 10/2003 | Fuchs et al. | |
| 2003/0221200 A1 | 11/2003 | McLachlan | |
| 2004/0052860 A1 | 3/2004 | Reid et al. | |
| 2004/0162414 A1 | 8/2004 | Santora et al. | |
| 2004/0241664 A1 | 12/2004 | Dekker et al. | |
| 2005/0164340 A1 | 7/2005 | Schlothauer et al. | |
| 2005/0175622 A1 | 8/2005 | Edens et al. | |
| 2006/0115538 A1 | 6/2006 | Krauskopf et al. | |
| 2006/0234942 A1 | 10/2006 | Tauzin et al. | |
| 2007/0092632 A1 | 4/2007 | Kubow et al. | |
| 2007/0116802 A1 | 5/2007 | Germano | |
| 2007/0148307 A1 | 6/2007 | Sherwood et al. | |
| 2007/0243231 A1 | 10/2007 | Krauskopf et al. | |
| 2009/0123952 A1 | 5/2009 | Slemmon | |
| 2010/0048464 A1 | 2/2010 | Recio Sanchez et al. | |
| 2010/0056458 A1 | 3/2010 | Cadee et al. | |

FOREIGN PATENT DOCUMENTS

| | | |
|---|---|---|
| DE | 296 23 285 U1 | 3/1998 |
| DE | 198 54 749 A1 | 5/2000 |
| DE | 100 08 880 A1 | 8/2000 |
| DE | 101 35 493 A1 | 1/2003 |
| DE | 102 33 229 A1 | 2/2004 |
| EP | 0 591 857 A1 | 4/1994 |
| GB | 2 013 495 A | 8/1979 |
| GB | 2 013 496 A | 8/1979 |
| JP | 54-113409 A | 9/1979 |
| JP | 54-113442 A | 9/1979 |
| JP | 62-63553 A | 3/1987 |
| JP | 6-192079 A | 7/1994 |
| JP | 63-87944 A | 4/1998 |
| JP | 2002-37738 A | 2/2002 |

(Continued)

OTHER PUBLICATIONS

U.S. Appl. No. 12/376,146.*
Brown, M.S. et al., "Drugs Used in the Treatment of Hyperlipoproteinemias" Goodman and Gillman's The Pharmacological Basis of Therapeutics Chapter 34, 7th Edition , MacMillan Publishing Co., New York (1985) pp. 827-845.
Daali, Y. et al., "Capillary Electrophoresis and High-Performance Anion Exchange Chromatograpgy for Monitoring Caseinoglycomacropeptide Sialylation" Journal of Pharmaceutical and Biomedical Analysis (2001) pp. 849-856, vol. 24.
Delaney, C.A. et al., "Sensitivity of Human Pancreatic Islets to Peroxynitrite-Induced Cell Dysfunction and Death" FEBS Letters (1996) pp. 300-306, vol. 394.
Fox, P.F., (Ed.)., "Developments in dairy chemistry-3: Lactose and minor constituents", Elsevier Applied Science Publishers; New York, NY (1982) pp. ii-v, vii-x, and 26-27.

(Continued)

*Primary Examiner* — Ruth Davis
(74) *Attorney, Agent, or Firm* — Scully Scott Murphy and Presser

(57) ABSTRACT

The invention relates to the use of whey permeate, preferably sweet whey permeate and more preferably hydrolysed or partially-hydrolysed sweet whey permeate for the production of a pharmaceutical composition for prophylaxis or treatment of symptoms of metabolic syndrome, type-2 diabetes and secondary diseases, said composition being provided for a mammal.

19 Claims, 15 Drawing Sheets

(56) References Cited

FOREIGN PATENT DOCUMENTS

| RU | 2005 128 653 A2 | 3/2007 |
|---|---|---|
| WO | 01/37850 A2 | 5/2001 |
| WO | 03/011263 A2 | 2/2003 |
| WO | 03/105882 A1 | 12/2003 |
| WO | 2004/009070 A1 | 1/2004 |
| WO | 2004/056207 A1 | 7/2004 |
| WO | 2005/000325 A2 | 1/2005 |
| WO | 2005/004990 A1 | 1/2005 |

OTHER PUBLICATIONS

International Search Report dated Nov. 30, 2004.
Jänner, "Report of the Expert Panel on Detection, Evaluation and Treatment of High Blood Cholesterol in Adults" U.S. Department of Health and Human Services, NIH Publication No. 89-2925 (1989) pp. 74-77.
Kawase, et al., "Effect of Administration of Fermented Milk Containing Whey Protein Concentrate to Rats and Healthy Men on Serum Lipids and Blood Pressure", Journal of Dairy Science, American Dairy Science Association, Champaign, Illinois, vol. 83, No. 2, Feb. 2000, pp. 255-263.
Klupsch, H. J., "Saure Milcherzeugnisse, milchmischgetränke und desserts 2. Auflage" Verlag Th. Mann Germany (1992) pp. 175-178.
Pschyrembel, Klinisches Wörterbuch (1994) 257 Edition, pp. 321.
Reaven, G.M., "Do High Carbohydrate Diets Prevent the Development or Attenuate the Manifestations (or both) of Syndrome X? A Viewpoint Strongly Against" Current Opinion in Lipidology(1997) pp. 23-27, vol. 8(1).
Roche Lexikon Medizin, 4th Edition, published by Urban & Fischer Verlag (1999).
Scheme titled "Membranverfahren, Trennbereiche verschiedener Membranen" (Membrane processes, separation areas of various membranes) identifying "Proteine" (proteins) and "Makromoleküle" (other macro molecules), Institute for Technical Conservation, Feb. 2010.
Schlimme, E., (Ed.)., "Kompendium zur milchwirtschaftlichen chemie", VV—GmbH Volkswirtschaftlicher Verlag Miinchen, München, Germany (1990) pp. 106, 108, and 136 37.
Sienkiewicz, T., & Riedel, C., "Whey and whey utilization" Gelsenkirchen Buer, Verlag Th. Mann, Germany (1990) pp. 3, 4, 11, 12, 50, 261, 262, 331, 255, 368, 371 73, and 377 78.
Soergel, K., "Acute Pancreatitis in Gastrointestinal Disease" Chapter 91, 3rd Edition, (Sleisenger, M.H. and Fordtran, J.S. eds) W.B. Saunders Company, Philadelphia, PA (1983) pp. 1462-1485.
Tanne, D. et al., "Blood Lipids and First-Ever Ischemic Stroke/Transient Ischemic Attack in the Bezafibrate Infarction Prevention (BIP) Registry" Circulation (2001) pp. 2892-2897, vol. 104.
The Diabetes Atorvastatin Lipid Intervention (DALI) Study Group, "The Effect of Aggressive Versus Standard Lipid Lowering by Atorvastatin on Diabetic Dyslipidemia" Diabetes Care (2001) pp. 1335-1341, vol. 24.
Vega, G.L. et al., "Pathogenesis of Hypertriglyceridemia: Implications for Coronary Heart Disease and Theraphy" Advances Experimental Medicin (1989) pp. 311-326, vol. 243.
Yu-Jin Kim et al., Purification and characterization of human caseinomacropeptide produced by a recombinant Saccharomyces cerevisiae, 41 Protein Expression & Purification 441 (2005).
Barile, D., et al., 2009, "Permeate from cheese whey ultrafiltration is a source of milk oligosaccharides", International Dairy Journal, vol. 19, No. 9, pp. 524-530.
Bounous, G., et al., 2000, "Whey protein concentrate and glutathione modulation in cancer treatment", Anticancer Research, vol. 20, No. 6C, pp. 4785-4792.
Bounous, G., et al., 2003, "The antioxidant system", Anticancer Research, vol. 23, No. 28, pp. 1411-1415.
Carles, C., et al., 1986, "Determination of gradient elution conditions for the separation of peptide mixtures by reversed-phase high-performance liquid chromatography: bovine 13-casein tryptic digest", Journal of Dairy Research, vol. 53, pp. 595-600.
Dallas, D. C., et al., 2014, "Coupling mass spectrometry-based "Omic" sciences with bioguided processing to unravel milk's hidden bioactivities", Journal of Advanced Dairy Research, vol. 1, No. 2, pp. 104-126.
Espeja, E., et al., 2001, "Fast detection of added soybean proteins in cow's, goat's, and ewe's milk by perfusion reversed-phase high-performance liquid chromatography", Journal of Separation Science, vol. 24, Nos. 10-11, pp. 856-864.
Ferreira, I., et al., 2003, "Detection and quantification of bovine, ovine and caprine milk percentages in protected denomination of origin cheeses by reversed-phase high-performance liquid chromatography of betalactoglobulins", Journal of Chromatography A, vol. 1015, Nos. 1-2, pp. 111-118.
Ferreira, I., et al., 2003, "Determination of caseinomacropeptide by an RP-HPLC method and monitoring of the addition of rennet whey to powdered milk", Journal of Liquid Chromatography & Related Technologies, vol. 26, No. 1, pp. 99-107.
Garcia, M. C. et al., 1997, "Simultaneous separation of soya bean and animal whey proteins by reversed-phase high performance liquid chromatography: Quantitative analysis in edible samples", Analytical Chemistry, vol. 69, No. 11, pp. 2217-2220.
Garcia, M. C., et al., 1998, "Ultrarapid detection of bovine whey proteins in powdered soybean milk by perfusion reversed-phase high-performance liquid chromatography", Journal of Chromatography, A, vol. 822, No. 2, pp. 225-232.
Hearn, M. T. W., et al., 1988, "High-performance liquid chromatography of amino acids, peptides and proteins. LXXXVII. Comparison of retention and bandwidth properties of proteins eluted by gradient and isocratic anion-exchange chromatography", Journal of Chromatography, vol. 458, No. 1, pp. 27-44.
International Preliminary Report on Patentability issued in International Application No. PCT/EP2007/058073 dated Feb. 17, 2009.
Jung, Y. A, et al., 2003, "Mobile phase composition for resolving whey proteins in reversed-phase high performance liquid chromatography", Korean Journal of Chemical Engineering, vol. 20, No. 4, pp. 705-708.
Kent, K. D., et al., 2003, "Effect of whey protein isolate on intracellular glutathione and oxidant-induced cell death in human prostate epithelial cells", Toxicology In Vitro, vol. 17, No. 1, pp. 27-33.
Krusa, M., et al., 2000, "A reversed-phase high-performance liquid chromatographiC method for the determination of soya bean proteins in bovine milks", Analytical Chemistry, vol. 72, No. 8, pp. 1814-1818.
Lipatov, N., 1973, "New physical methods for processing dairy products", Annual Bulletin-International Dairy Federation, No. 75, pp. 1-12.
Lothian, B., et al., 2000, "Treatment of obstructive airway disease with a cysteine donor protein supplement", Chest, vol. 117, pp. 914-916.
Macleod, A., et al. "Separation of β-lactoglobulin variants A and B from cheese whey by biospecific subunit exchange affinity chromatography" Milchwissenschaft 50 (8):440-444 (1995).
Mant, C. T., et al., 1987, "Optimization of peptide separations in reverse-phase HPLC: Isocratic versus gradient elution", Chromatographia, vol. 24, pp. 565-572.
Marshall, K., 2004, "Therapeutic applications of whey protein", Alternative Medicine Review, vol. 9, No. 2, pp. 136-155.
Michaelidou, A., et al., 1998, "Isolation and identification of some major water-soluble peptides in feta cheese", Journal of Dairy Science, vol. 81, No. 12, pp. 3109-3116.
Moatsou, G., et al., 2003, "Nitrogenous fractions during the manufacture of whey protein concentrates from feta cheese whey", Food Chemistry, vol. 81, No. 2, pp. 209-217.
Monaci, L., et al., 2009, "Mass spectrometry-based proteomics methods for analysis of food allergens", Trends in Analytical Chemistry, vol. 28, No. 5, pp. 581-591.
Moreno, Y. F., et al., 2005, "Features of whey protein concentrate supplementation in children with rapidly progressive HIV infection", Journal of Tropical Pediatrics, vol. 52, No. 1, pp. 34-38.

(56) References Cited

OTHER PUBLICATIONS

Mota, M. V. T, et al., 2004, "Enzymatic hydrolysis of whey protein concentrates: Peptide HPLC profiles", Journal of Liquid Chromatography & Related Technologies, vol. 27, No. 16, pp. 2625-2639.

Muthukumaran, S., et al. "Mechanisms for the ultrasonic enhancement of dairy whey ultrafiltration" Journal of Membrane Science 258:106-114 (2005).

Nueu, Uwe, D., HPLC troubleshooting guide, www.waters.com/webassets/cms/library/docs/wa20769.pdf, American Laboratory and Waters Corporation (2002) accessed on Jan. 30, 2013.

Smithers, G. W., et al., 1996, "New opportunities for the isolation and utilization of whey proteins", Journal of Dairy Science, vol. 79, pp. 1454-1459.

Taylor, M. J. et al., "Antioxidant Acitvity of Skim Milk: Effect of Heat and Resultant Sulfhydryl Groups" J Dairy Sci, 63:1783-1795 (1980).

Taylor, M. J. et al., Antioxidant Acitvity of Skim Milk: Effect of Sinication J Dairy Sci, 63:1938-1942 (1980).

Tong, L. M., 2000, "Antioxidant activity of whey in a salmon oil emulsion", Journal of Food Science, vol. 65, No. 8, pp. 1325-1329.

Tong, L. M., et al., 2000, "Mechanisms of the antioxidant activity of a high molecular weight fraction of whey", Journal of Agriculture and Food Chemistry, vol. 48, pp. 1473-1478.

Tseng, Y.-M., et al., 2006, "Whey protein concentrate promotes the production of glutathione (GSH) by GSH reductase in the PC12 cell line after acute ethanol exposure", Food and Chemical Toxicology, vol. 44, pp. 574-578.

Villamiel, M., et al., 2000, "Influence of high-intensity ultrasound and heat treatment in continuous flow on fat, proteins, and native enzymes of milk", Journal of Agricultural Food Chemistry, vol. 48, No. 2, pp. 472-478.

Watanabe, A., et al., 2000, "Nutritional therapy of chronic hepatitis by whey protein", Journal of Medicine, vol. 31, Nos. 5-6, pp. 283-302.

Yamamoto, N., et al., 1999, "Purification and characterization of an antihypertensive peptide from a yogurt-like product fermented by Lactobacillus helveticus CPN4", Journal of Dairy Science, vol. 82, No. 7, pp. 1388-1393.

Zhang N. T. et al., 2002, "Isolation of lactoferrin from bovine colostrum by SP-Sepharose cation-exchange chromatography", Milchwissenschaft, vol. 57, Nos. 11-12, pp. 614-617.

Zommara, M., et al., 1996, "Whey from cultured skim milk decreases serum cholesterol and increases antioxidant enzymes in liver and red blood cells in rats", Nutritional Research, vol. 16, pp. 293-302.

Kosikowski and Wierzbicki, received for publication Jul. 31, 1972, Journal of Diary Science 56:1.

Maxilact® Product sheet, Gist-Brocades BSD B.V., Diary Ingredients Group.

Mertens and Huyghebaert, Milchwissenschaft, 1987, 42:640-642, 645.

Prenosil et al., 1987, Biotechnology and Bioengineering, 30:1026-1031.

Shah and Jelen, Milchwissenschaft, 1987, 42(12): 782-786.

TetraPak, Handbuch der Milch- und Molkereitechnik, 2003, Verlag Th. Mann GmbH & Co. KG, "Umwandlung von Laktose", Seiten 3, 12, 385-387 mit Deckseite.

* cited by examiner

Fig. 1: Feed and drink intake in the observation period
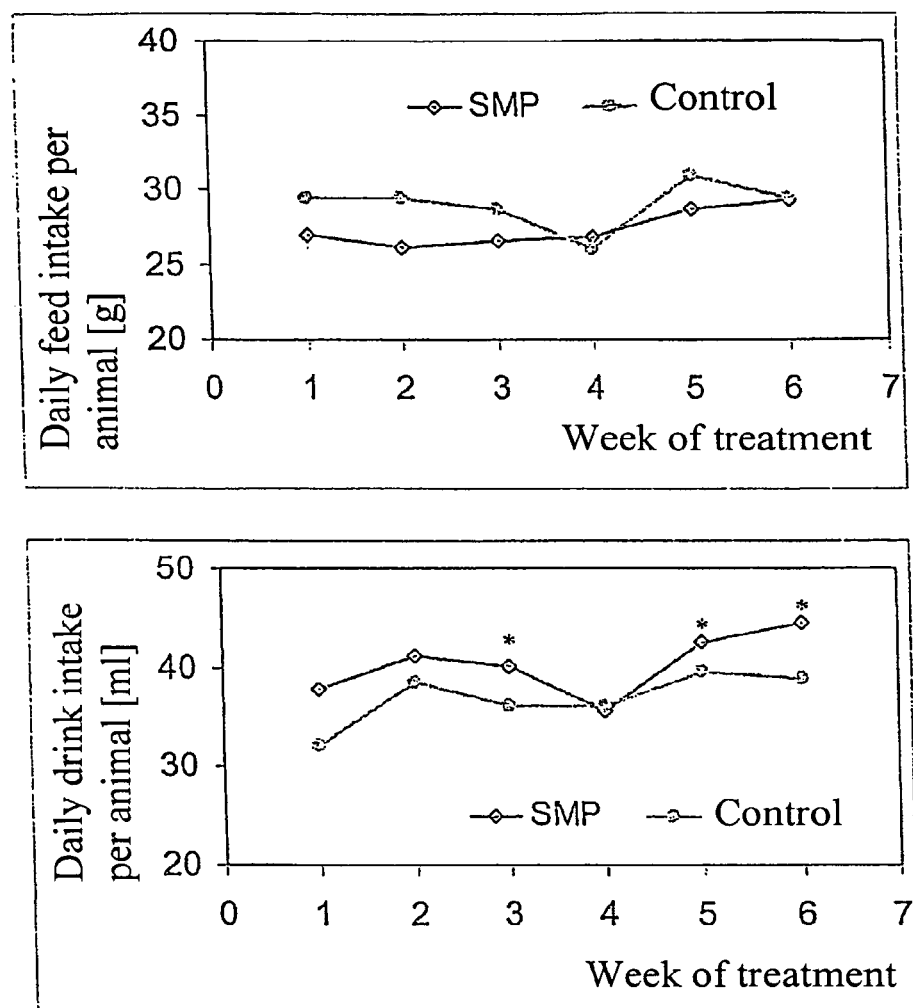
* p<0.05 vs. control Fig. 2: Body mass and blood glucose concentration in the observation period (7 days before the start of treatment and up to 42 days of treatment)
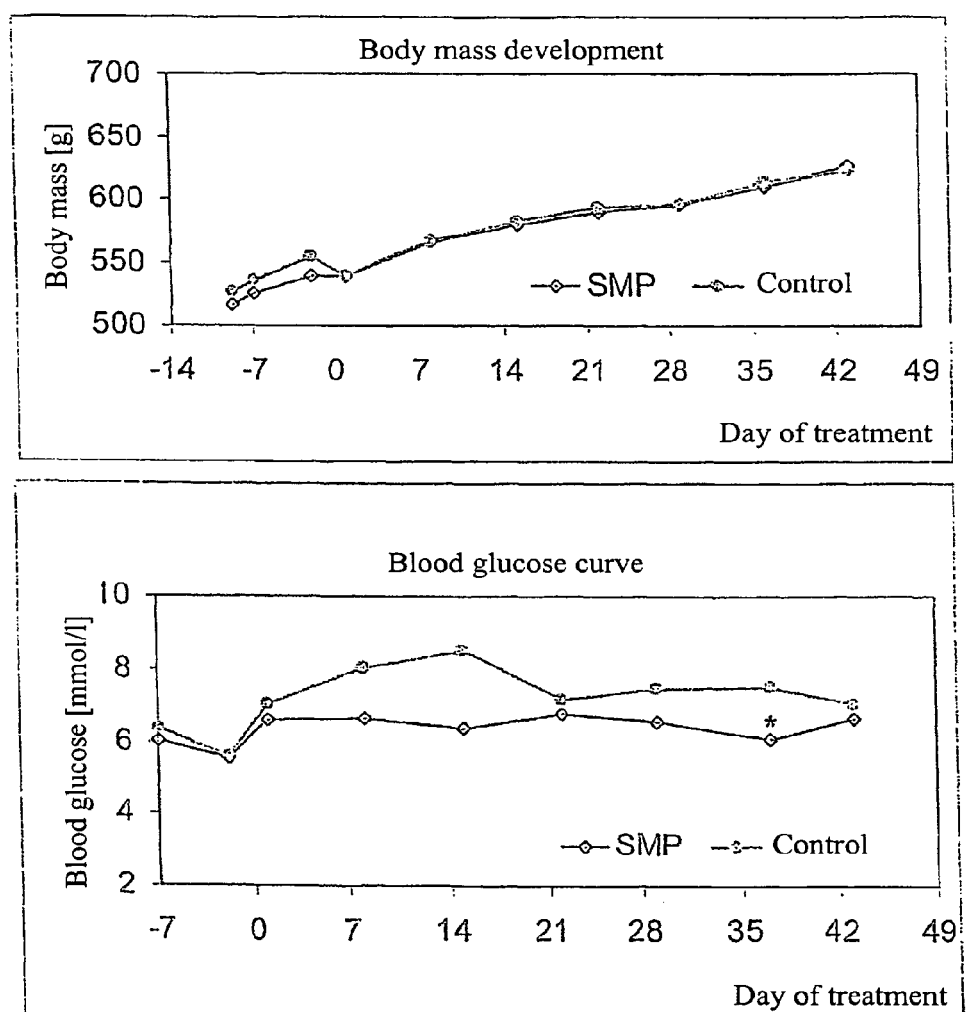
* $p<0.05$ vs. control Fig. 3a: Concentration of NEFA (non-esterified fatty acids) and insulin before the start of treatment, after 3 weeks and after 6 weeks of treatment $_{mean \pm SD}$
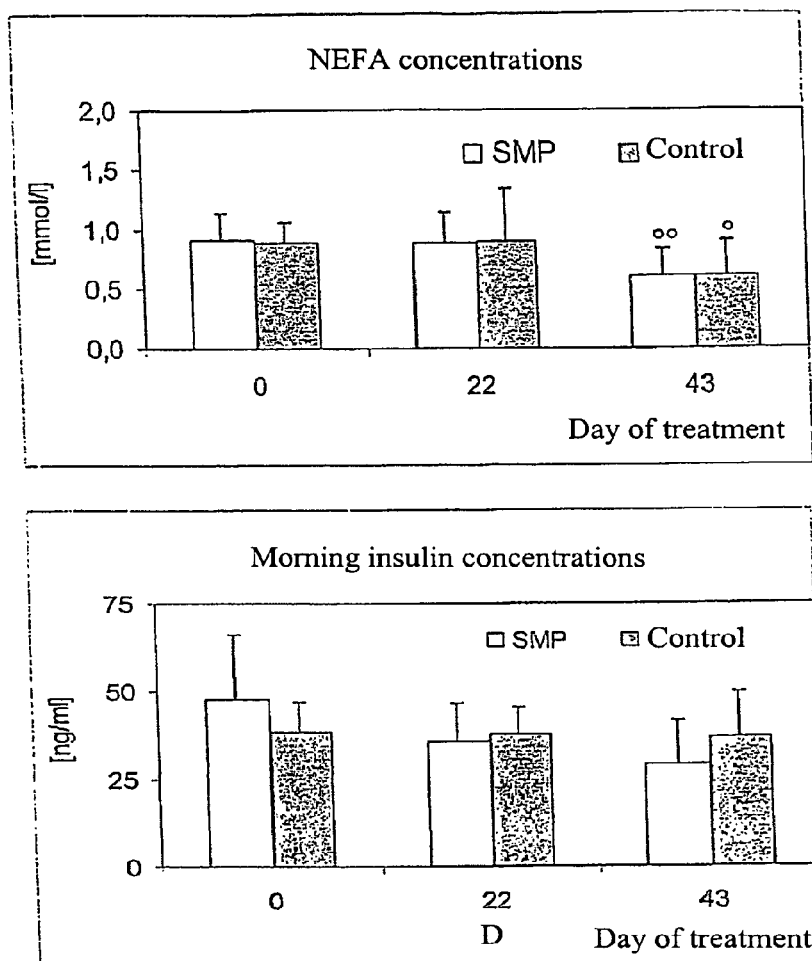
° p<0.05 vs. day 0
°° p<0.01 vs. day 0

Fig. 3b: Concentrations of total and HDL cholesterol before the start of treatment, after 3 weeks and after 6 weeks of treatment, mean ± SD
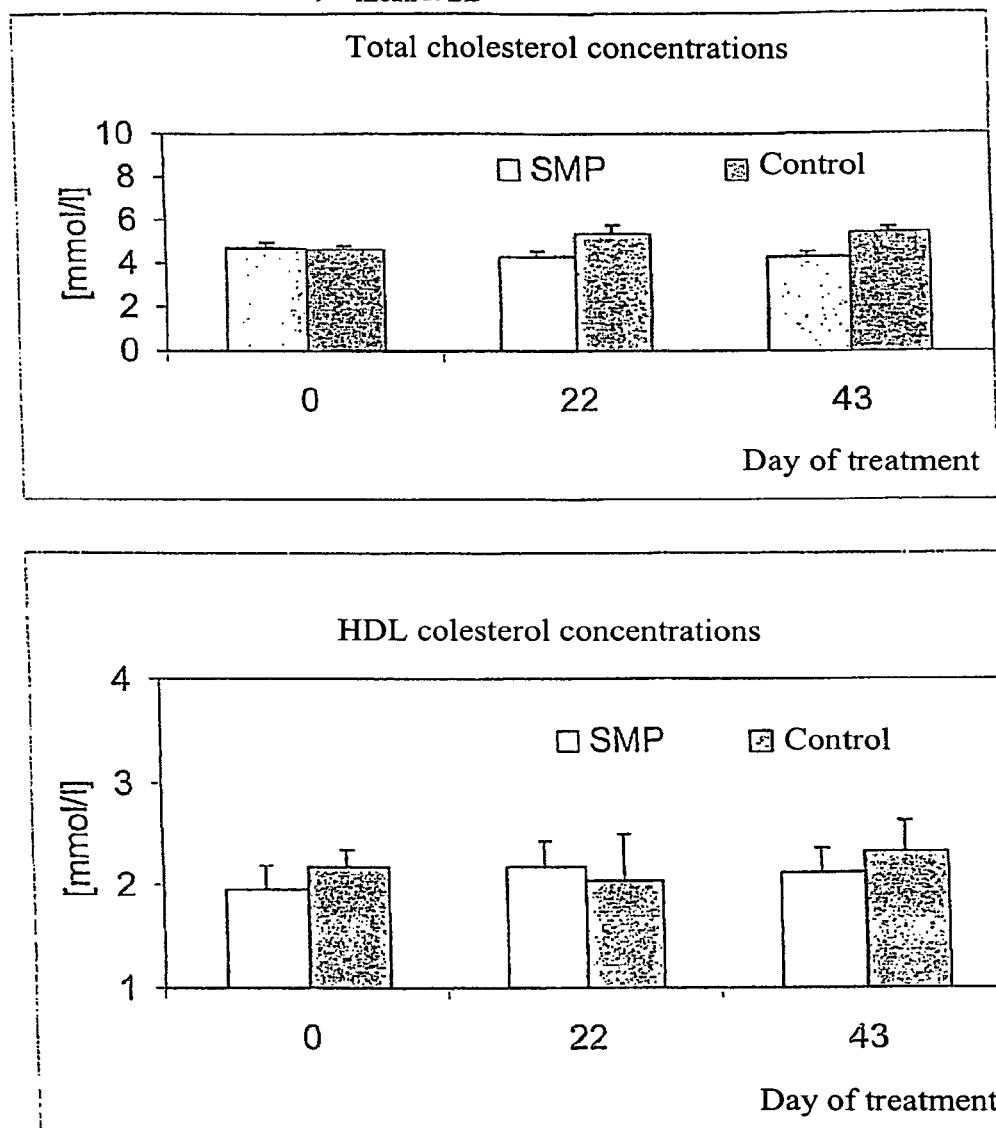

Fig. 3c: Concentrations of LDL cholesterol and triglycerides before the start of treatment, after 3 weeks and after 6 weeks of treatment
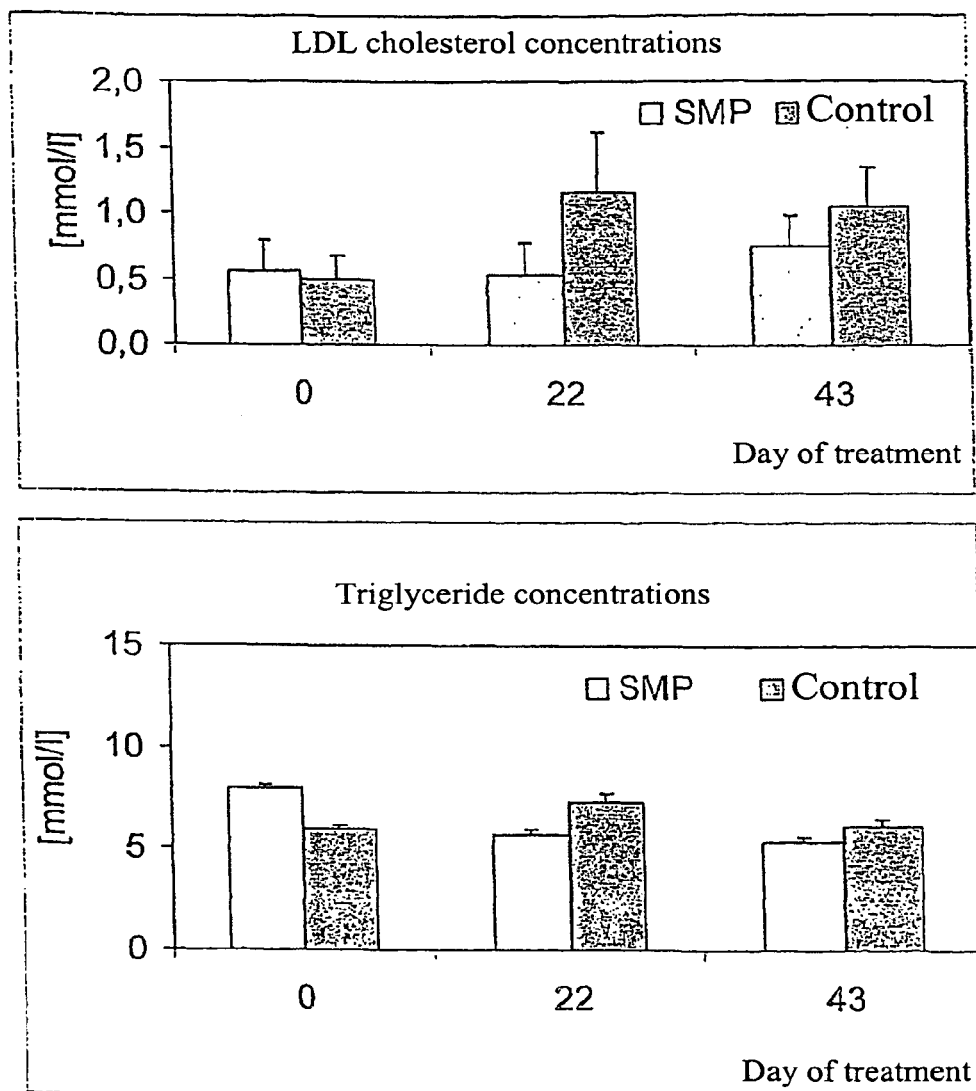

Fig. 3d: Concentrations of C-reactive protein before the start of treatment, after 3 weeks and after 6 weeks of treatment, mean ± SD
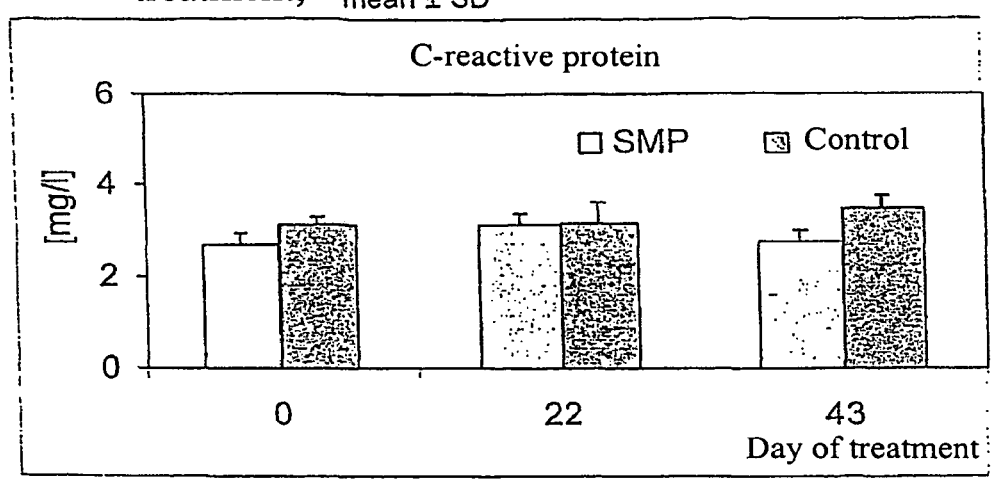

Fig. 3e: Number of leucocytes in 6-week observation period
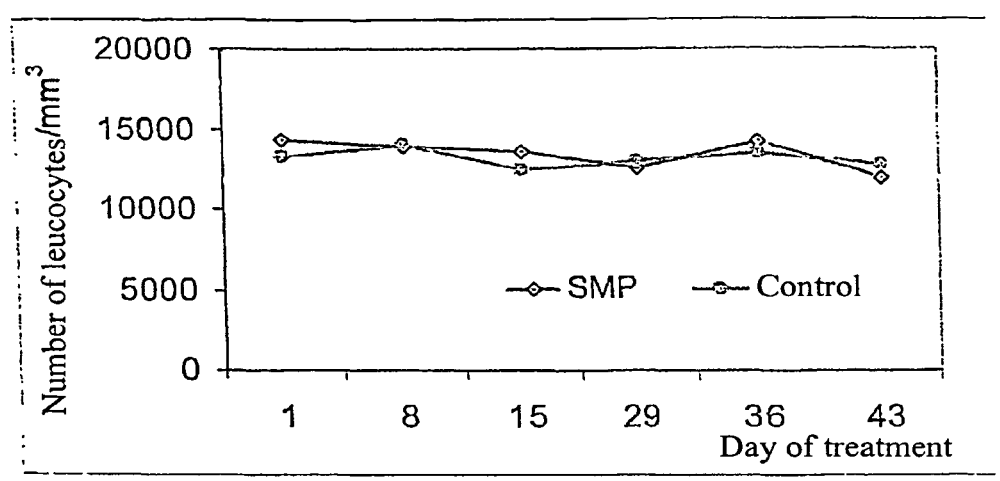

Fig. 4a: Blood glucose curve in the oGTT and glucose excess areas before the start of treatment
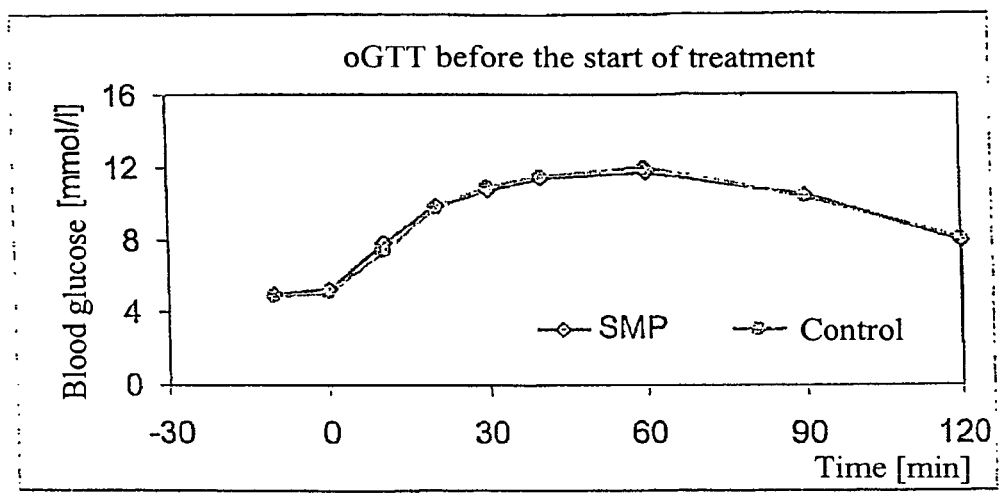
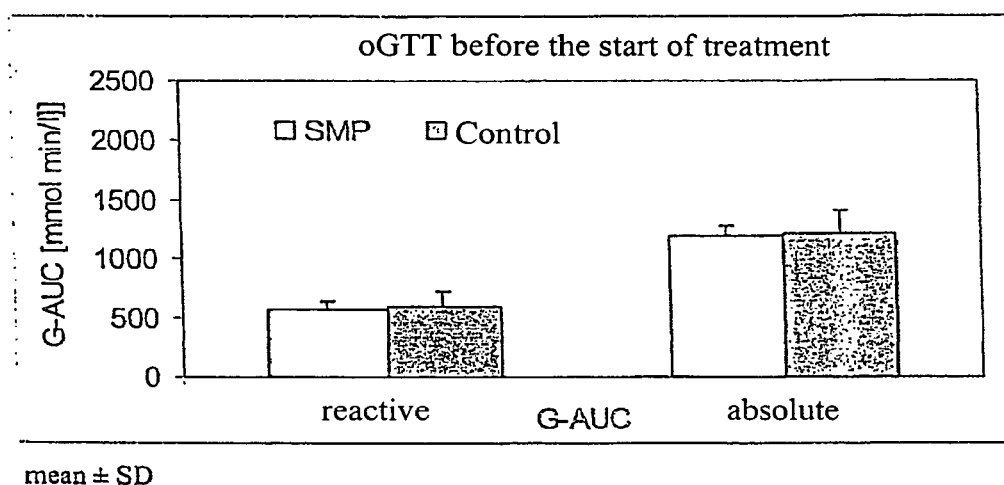
mean ± SD Fig. 4b: Curve of the insulin concentrations in the oGTT and insulin excess areas before the start of treatment
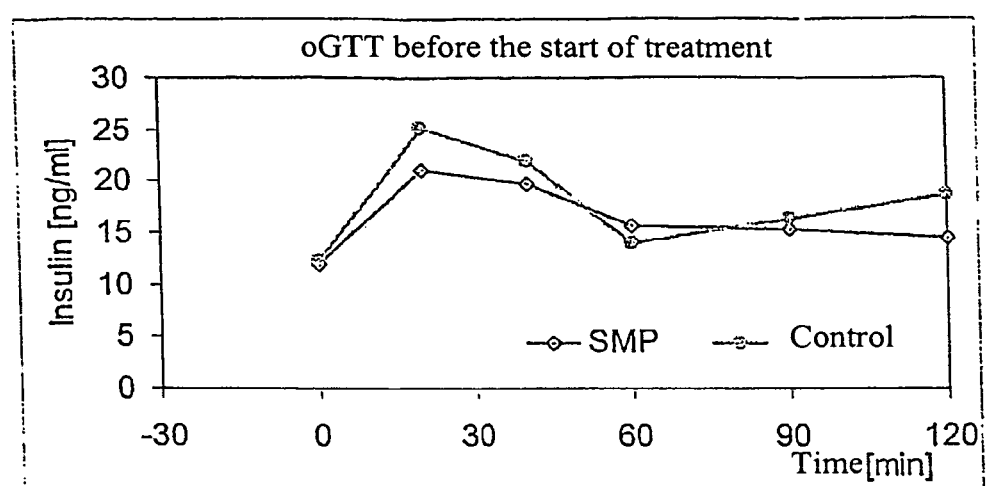
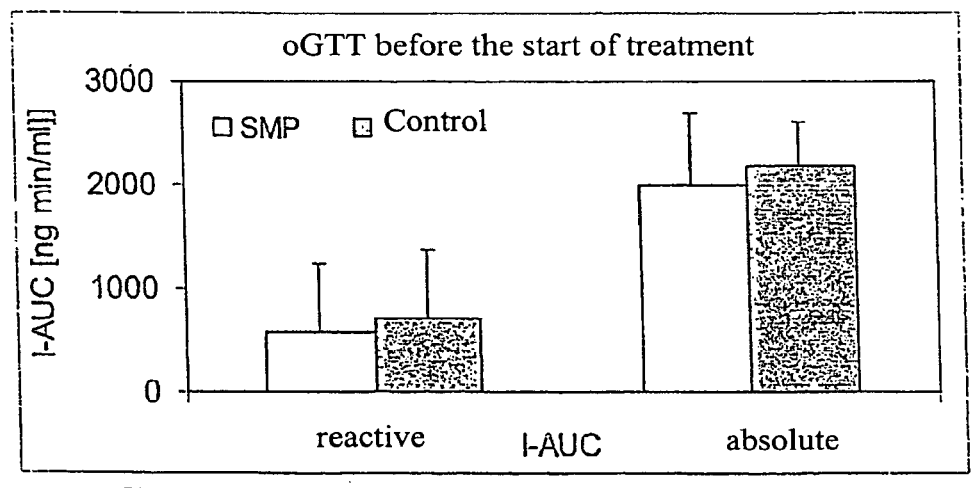
mean ± SD Fig. 5a: Blood glucose curve in the oGTT and glucose excess areas after 3 weeks of treatment
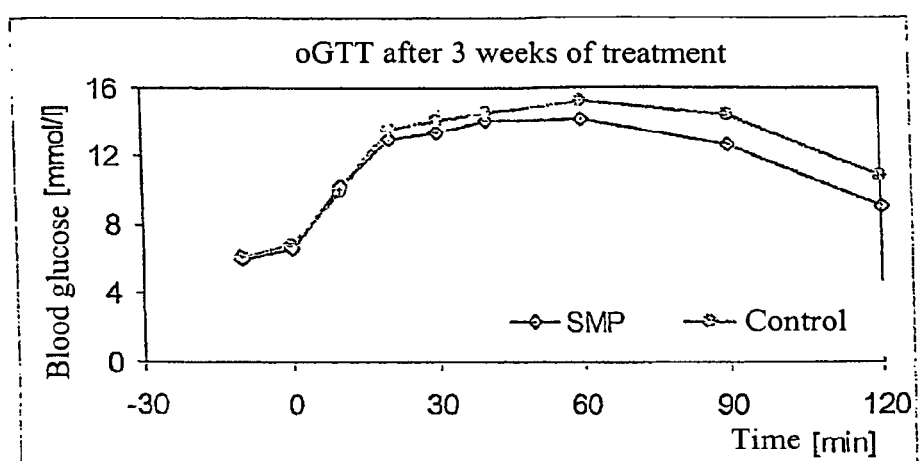
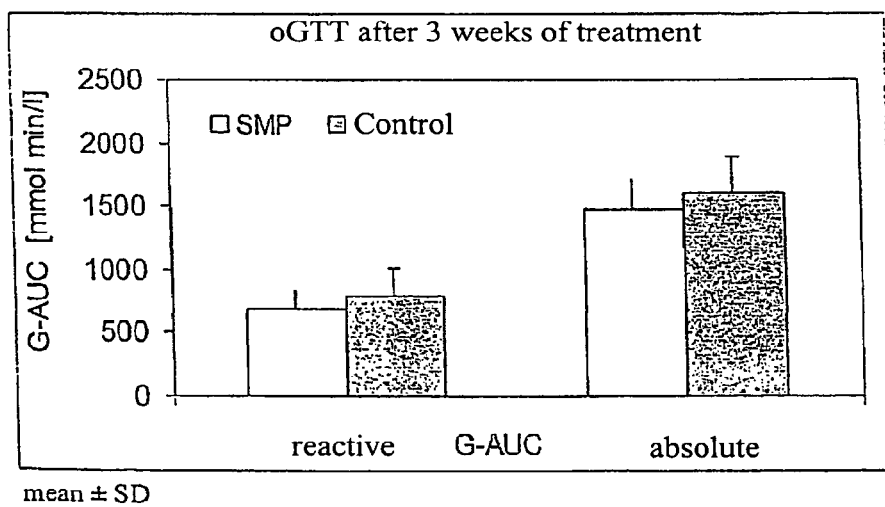
mean ± SD Fig. 5b: Curve of the insulin concentrations in the oGTT and insuline excess areas after 3 weeks of treatment
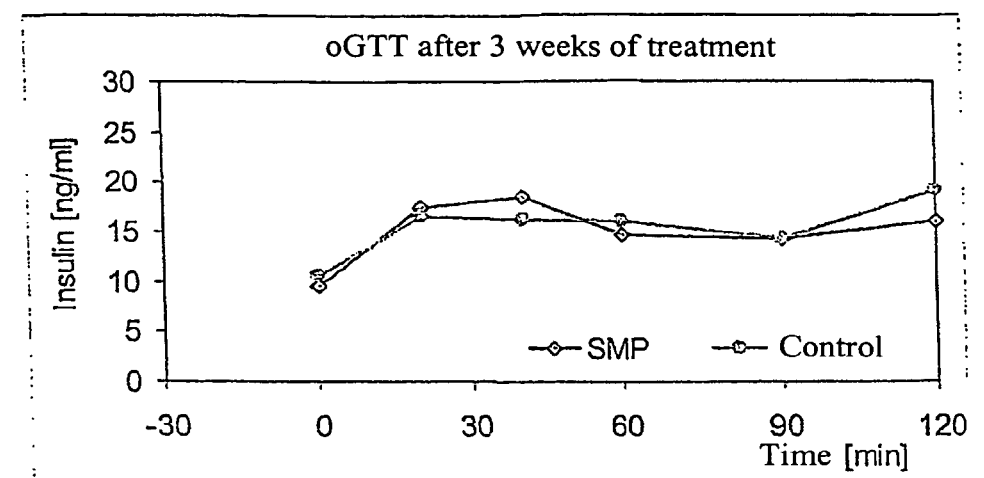
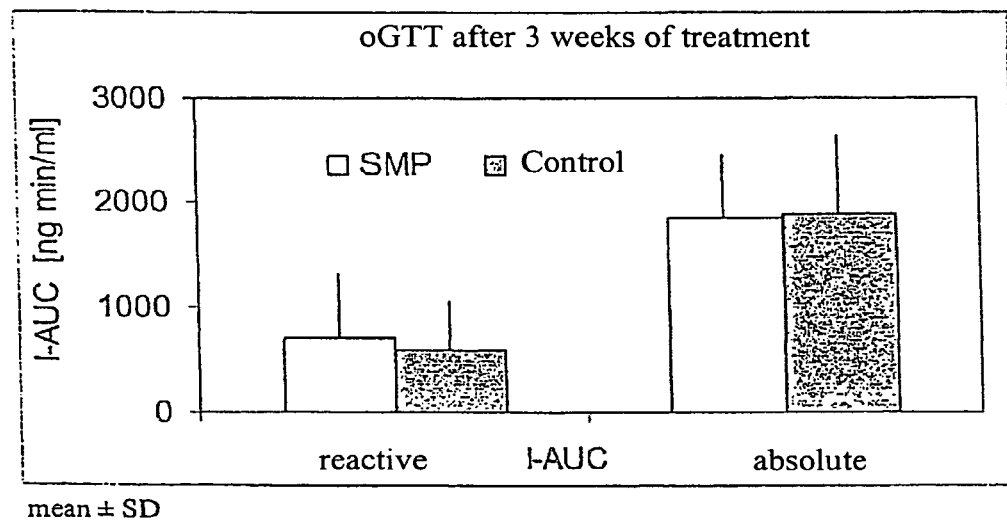
mean ± SD Fig. 6a: Blood glucose curve in the oGTT and glucose excess areas after 6 weeks of treatment
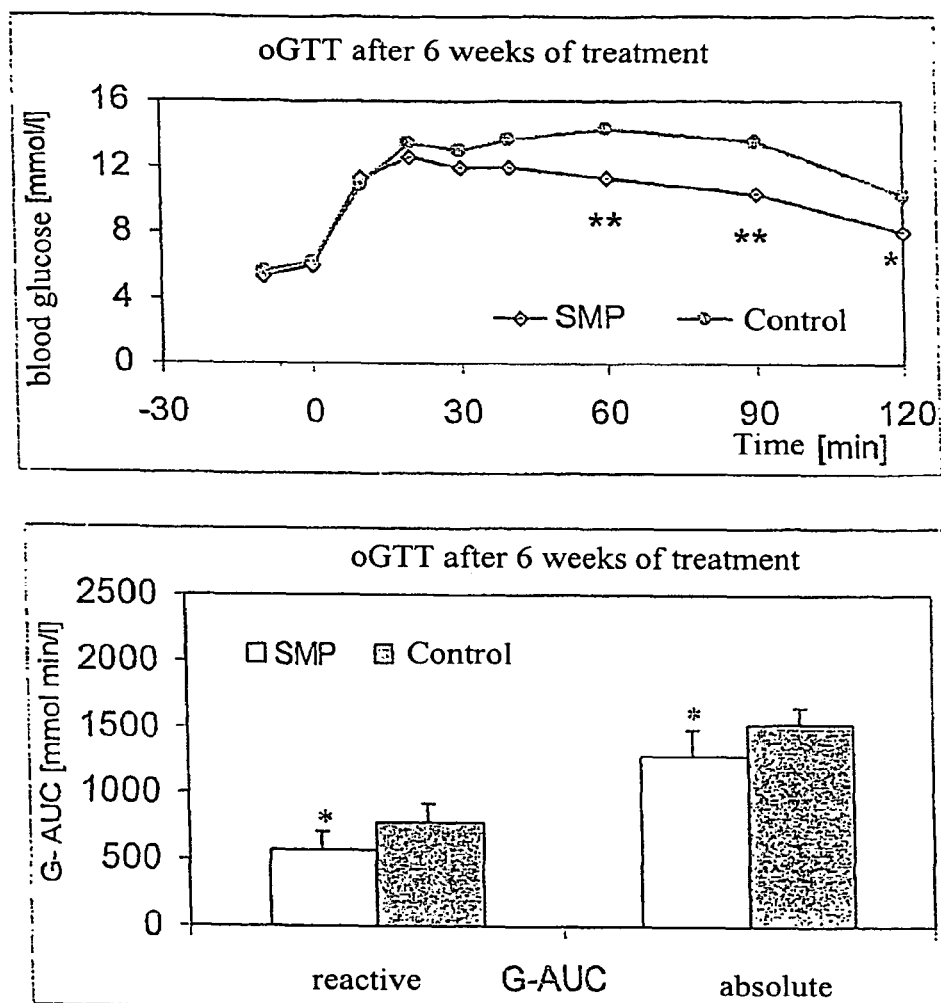
mean ± SD  * p<0.05 vs. control
          ** p<0.01 vs. control Fig. 6b: Curve of the insulin concentrations in the oGTT and insulin excess areas after 6 weeks of treatment
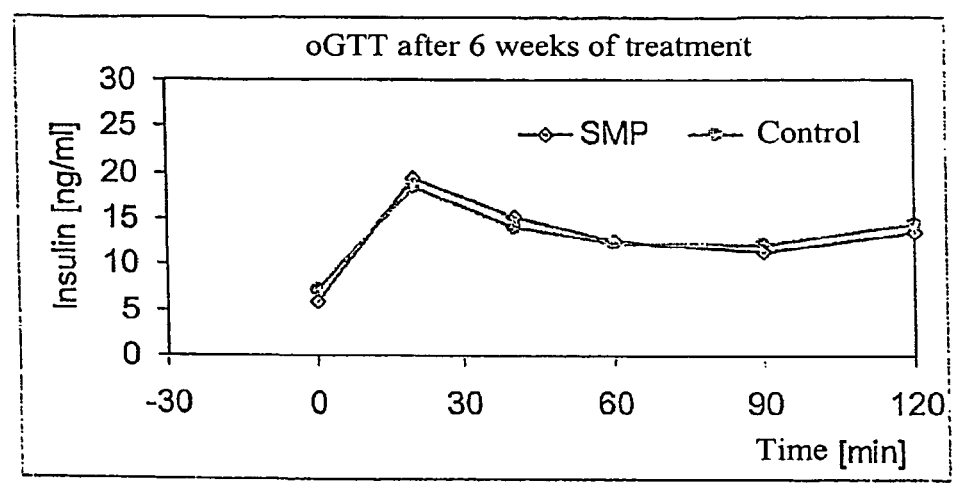
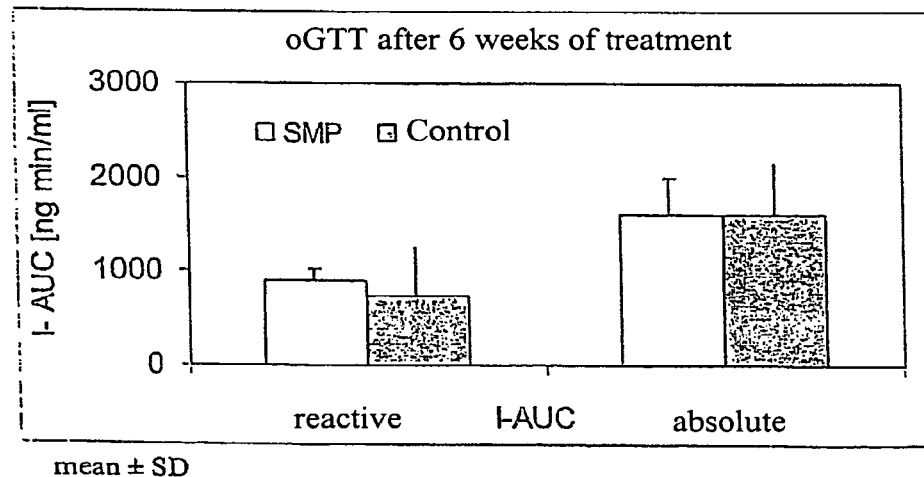
mean ± SD Fig. 7: Diurnal glood glucose and lactate profile before the start of treatment
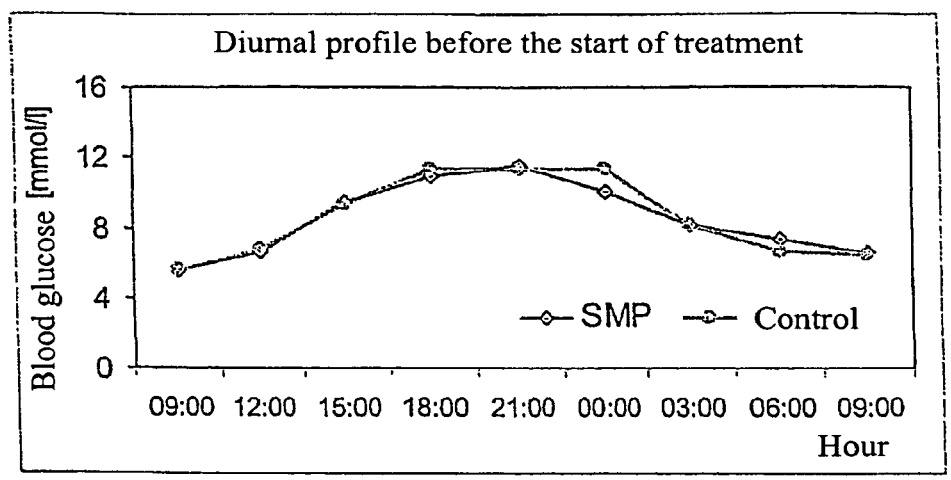
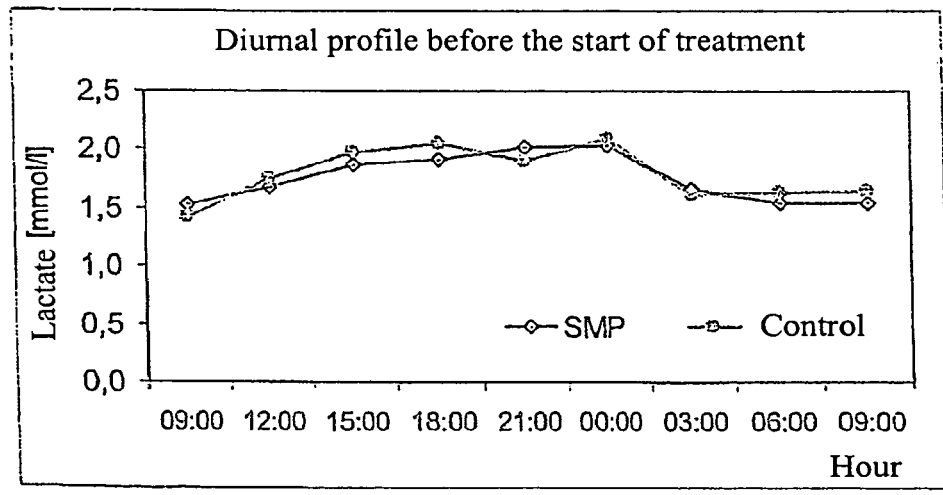

Fig. 8 : Diurnal blood glucose and lactate profile after 6 weeks of treatment
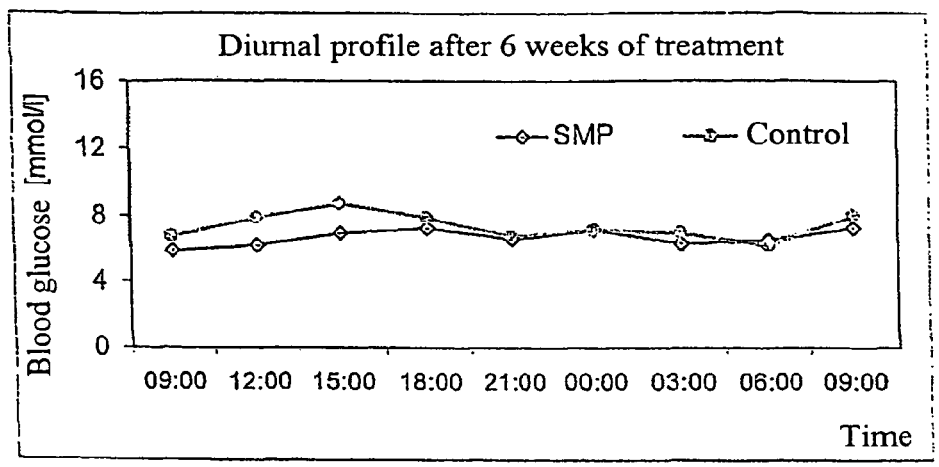
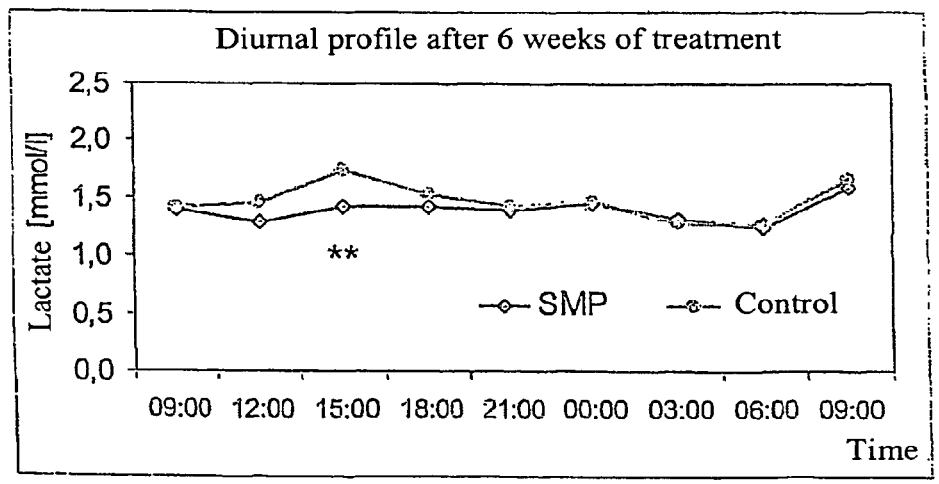
** p<0.01 vs. control

USE OF WHEY PERMEATE FOR THE TREATMENT OF METABOLIC SYNDROME

CROSS REFERENCE TO RELATED APPLICATION

The present application is a continuation application of U.S. application Ser. No. 10/564,075, filed Jan. 10, 2006, the entire contents of which are incorporated herein by reference.

TECHNICAL FIELD

The present invention relates to the treatment of metabolic syndrome or type 2 diabetes. Further disclosed is the use of whey permeate for producing dietary and pharmaceutical compositions for the prevention and treatment of symptoms of metabolic syndrome or type 2 diabetes.

PRIOR ART

According to WHO criteria, 63% of all men and 55% of all women in industrialized countries are overweight. Cause of this alarming development is caloric overnutrition with carbohydrates and fats with further reduction of the daily energy release. Even very small differences in the daily energy balance have a large cumulative effect on body mass over the years. A daily caloric input of 0.3% above the caloric consumption thus leads to a gain in weight of 9.1 kg in 25- to 55-year-old Americans. The overweight individuals frequently develop a metabolic syndrome (Reaven G M, Curr. Opin. Lipidol., 1997, 8 (1), p. 23-27).

In connection with the use of the term "metabolic syndrome" health professionals usually speak of the so-called "deadly quartet" which consists of overweight (obesity), high blood pressure, elevated insulin level and lipid metabolism disorder. In technical literature, the metabolic syndrome is also referred to as the first early syndrome or "prediabetes" ("*Pschyrembel, Klinisches Wörterbuch*", 257$^{th}$ ed. (1994), p. 321).

Those skilled in the art understand "syndrome" to mean a complex of symptoms; a group of disease signs (symptoms) characteristic of a certain clinical picture with mostly inconsistent or unknown etiology and/or pathogenesis.

Type 2 diabetes frequently develops as the metabolic syndrome further deteriorates. Increase in blood sugar is the most perspicuous feature hereof. Furthermore, these diseases promote an increased risk of secondary diseases such as arteriosclerosis. Further health risks caused by the pathological changes associated with diabetes are eye complaints, heart and vascular diseases, stroke, heart attack, kidney diseases, etc.

In the past decades, the frequency of type 2 diabetes has increased considerably. The German Federal Office of Statistics estimates that approximately four million people in Germany are currently affected. Other studies, however, assume considerably higher numbers. According to estimates of the German Diabetes Society, one in ten Germans will be affected by type 2 diabetes in 2006. The blood lipid levels (cholesterol, triglycerides) and blood pressure of overweight diabetics are also usually increased.

Contrary to type 1 diabetes, insulin is indeed produced in type 2 diabetes. However, this cannot be properly utilized by the body. The insulin is formed in the pancreas and ensures that glucose from food enters the cells. When glucose from food is supplied to the body and the blood sugar level in the blood rises, an increased amount of insulin is delivered to the blood in order to transport glucose to the cells, thus causing the blood sugar level to drop again. Once the body no longer reacts properly to the insulin, the cells become insulin-resistant. According to Roche Lexikon Medizin, 4th edition, Urban & Fischer Publishers, 1999, insulin resistance is defined as the strong mitigation or the absence of a therapeutic effect of insulin. There are three explanations for the development of insulin resistance. Firstly, IgG antibodies may inhibit the biological efficiency of insulin, thereby increasing the daily demand to above 100 IU (International Units). Secondly, an increased enzymatic cleavage of insulin may occur, or, thirdly, binding of insulin to its receptors may be reduced. As a consequence, an insufficient amount of energy reaches the cells while the blood sugar level remains high. This causes the pancreas to release even more insulin to lower the blood sugar level. The constant overproduction of insulin leads to an exhaustion of the insulin-producing beta cells in the pancreas and finally to insulin deficiency.

Type 2 diabetics are frequently treated today with oral antidiabetics. These include:
a) drugs which delay the intake of carbohydrates, e.g. alpha glucosidase inhibitors,
b) biguanides—a group of substances which both delay sugar resorption and inhibit sugar neoformation in the liver. In addition, biguanides promote the uptake of sugar into the musculature and at the same time repress the appetite;
c) glitazones improve the sensitivity of the cells to insulin when this is still being produced—thereby lowering the blood sugar level efficiently;
d) glinides regulate the blood sugar after a meal by stimulating the short-term insulin release from the beta cells of the pancreas by a special mechanism,
e) sulfonylureas, which lower the blood sugar threshold, starting at which the beta cells of the pancreas release insulin.

Besides oral antidiabetics, it can become necessary that insulin is supplied to the patient. Here, individualized forms of therapy are carried out which are tailored to the needs of the patient.

The treatment of the metabolic syndrome substantially relies on the patient achieving a weight reduction by changing his eating habits and doing more exercise. However, additional drugs are often necessary to reduce blood pressure, blood sugar and blood lipids. Estimates concerning the costs incurred yearly in the USA by direct expenses and indirect costs through loss of productivity by the above-mentioned forms of treatment amount to a total of 98 billion dollars—and this is increasing.

Therefore it is necessary to provide means and ways for the prevention and treatment of metabolic syndrome or type 2 diabetes. Furthermore, means for preventing or delaying the deterioration of the symptoms as well as for relieving or curing them are required. Particularly, an improved treatment of metabolic syndrome is required in order to counteract further progression into type 2 diabetes.

In the following, the term "prevention" means that the development of a symptom or a disease is prevented. The term "treatment" means here each form of treatment for the improvement of the disease symptoms, the delay of the progression of the disease, the regression of the disease or the relief of the disease symptoms.

DESCRIPTION OF THE FIGURES

The following Figures show the results of animal experiments with sweet whey permeate for determining different parameters relevant for symptoms of metabolic syndrome or diabetes.

FIG. 1 shows the intake of feed and drink during the 6-week period of observation in animals treated with sweet whey permeate (SMP) and their controls.

FIG. 2 shows the development of body mass and the curve of blood glucose during the period of observation in animals treated with sweet whey permeate (SMP) and their controls.

FIG. 3(a) shows the concentration of non-esterified fatty acids (NEFA) and insulin in the blood of the experimental animals before initiation of the treatment, after 3 weeks and after 6 weeks of treatment with or without SMP.

FIG. 3(b) shows the concentration of total and HDL cholesterol in the blood of the experimental animals before initiation of the treatment, after 3 weeks and after 6 weeks of treatment with or without SMP.

FIG. 3(c) shows the concentration of LDL cholesterol and triglycerides in the blood of the experimental animals before initiation of the treatment, after 3 weeks and after 6 weeks of treatment with or without SMP.

FIG. 3(d) shows the concentration of C-reactive protein in the blood of the experimental animals before initiation of the treatment, after 3 weeks and after 6 weeks of treatment with or without SMP.

FIG. 3(e) shows the number of leucocytes of the experimental animals during the 6-week period of treatment when treated with or without SMP.

FIG. 4(a) shows the blood glucose curve in the oral glucose tolerance test (oGTT) and the glucose excess areas before initiation of the treatment.

FIG. 4(b) shows the curve of the serum insulin concentration in the oGTT and the insulin excess areas before initiation of the treatment.

FIG. 5(a) shows the curve of blood glucose in the oGTT and the glucose excess areas after 3 weeks of treatment.

FIG. 5(b) shows the curve of serum insulin concentration in the oGTT and the glucose excess areas after 3 weeks of treatment.

FIG. 6(a) shows the curve of blood glucose in the oGTT and the glucose excess areas after 6 weeks of treatment.

FIG. 6(b) shows the curve of serum insulin concentration in the oGTT and the glucose excess areas after 6 weeks of treatment.

FIG. 7 shows the diurnal profile of blood glucose and lactate before initiation of the treatment.

FIG. 8 shows the diurnal profile of blood glucose and lactate after 6 weeks of treatment.

DETAILED DESCRIPTION OF THE INVENTION

It has surprisingly been found that administration of whey permeate to animals recognized as models for metabolic syndrome and type 2 diabetes results in prevention of glucose intolerance and prevention of insulin resistance as well as in a lowering of the triglyceride concentration in the serum.

Thus, according to the invention, a pharmaceutical composition is provided comprising whey permeate. This pharmaceutical composition is used for the prophylaxis, treatment or prevention of hypertriglyceridemia, glucose intolerance and insulin resistance in metabolic syndrome or type 2 diabetes as well as in secondary diseases arising therefrom in mammals, preferably humans.

Examples of secondary diseases which accompany metabolic syndrome or diabetes are vascular diseases, coronary insufficiency, arterial occlusive diseases, myocardial infarction, xanthomas, abdominal discomfort, splenohepatomegaly, pancreatitis, retinal lipemia, and/or stroke.

Whey accumulates during the production of cheese from milk. According to the invention, cow milk, goat milk, sheep milk, buffalo milk and camel milk can be used for the extraction of whey after the casein present in the milk has precipitated. Depending on the type of extraction, a distinction is made between sweet whey, which develops as milk serum after enzymatic precipitation of casein by rennet, and acid whey, which is extracted after separating casein by acid precipitation. The pH boundary between sweet and acid whey is not very well defined and generally lies over or under a range of 5.6 to 5.9. Sweet whey is preferably used in the context of this invention.

The whey used according to the invention contains all watersoluble components of milk, unless these are precipitated by rennet or acid. In a particular embodiment, sweet whey is used containing about 4.9% lactose, 0.8% protein, 0.5% mineral substances, 0.2% milk fat, and 0.2% lactic acid.

By way of ultrafiltration (membrane procedure, average pore size: 25 to 100 kDalton), the whey protein can be separated from whey. This "dewhitened" whey consists of about 95% water and can be further processed to a powder by spray drying. This powder is herein referred to as whey permeate. In the present invention, the use of whey permeate extracted from sweet whey is preferred. The components contained on average therein are 84.9% lactose, 4.5% protein, 0.1% fat, and 7.5% mineral substances. The remainder is non-separated water. These amounts are average values which may vary by 5-10% (relative), depending on the manner of production. Whey permeate can be used as such or after (partial) hydrolysis of the lactose. Preferred forms of administration of the whey are as syrups or powders, but other forms of administration are also possible.

According to the invention hydrolyzed as well as partially hydrolyzed sweet whey permeate is used.

In a further embodiment of the invention, microencapsulation of the pharmaceutical composition comprising whey permeate has proven to be particularly advantageous. Microencapsulation can be effected as described, inter alia, in the patent laid-open publications DE 198 54 749 A1 and DE 100 08 880 A1 and the utility model DE 296 23 285 U1. The compound is firmly enclosed thereby, for example, in a coating consisting of a polysaccharide, such as alginate. A digestible component such as starch may be added to the coating so that the possibly indigestible covering substance does not prevent release of the compound, thereby rendering nutritional utilization by the organism impossible. Delivery of the microencapsulated pharmaceutical composition to different regions of the intestinal tract can thus be targetedly controlled by an adept selection and/or combination of the soluble and insoluble coating components. Stepwise release in the intestine, e.g. a release of 50 to 80% by weight, preferably 60 to 70% by weight, particularly 62.5% by weight, in the small intestine, and a release of 20 to 50% by weight, preferably 30 to 40% by weight, particularly 62.5% by weight, in the large intestine is a possible type of targeted release. A further advantageous effect can be achieved by prolonged durability by protecting the encapsulated compound from, e.g., environmental influences.

The use of the terms sweet whey or sweet whey permeate also includes all substances which can be extracted therefrom. These are proteins, sugars and their components, as well as mineral substances.

Furthermore, the use of sweet whey permeate is preferred, from which lactose has been partially or totally removed. This sweet whey permeate is referred to as lactose-reduced sweet whey permeate for the purposes of this invention.

Lactose-reduced sweet whey permeate usually contains about 85% lactose which can, however, be extracted therefrom for further use.

Thus, lactose-reduced sweet whey permeate remains which contains between 0.1 and 80%, preferably between 1 to 50%, more preferably between 5 and 25% lactose. Lactose-reduced sweet whey permeate still containing 10 to 20% lactose is particularly preferred.

The present invention further provides a preparation having the following effects, as also shown in the following examples:

lowering the serum insulin level,
preventing the development of glucose intolerance,
preventing insulin resistance,
lowering the volume of the pancreatic islets,
reducing the volume of the β cells in the pancreas,
preventing the neogenesis of β cells in the pancreatic duct epithelium,
preventing the development of hyperinsulinism,
preventing inflammation of the pancreas (pancreatitis) or a selective inflammation of the islets and/or β cells (insulitis).

A further object is the use of whey permeate for the prevention and/or treatment of type 2 diabetes, especially for delaying progression of the disease, preferably for improving the pathology thereof.

It has surprisingly been found according to the invention that a morphological correlate exists for hyperinsulinism. This means that the β cell volume increases, small clusters of β cells appear in the exocrine pancreas, β cells are detected in the epithelium of the pancreas duct (indication of a neogenesis) and the β cell mitosis rate increases. This morphological correlate suggests an increased demand on this organ which is partially compensated by a multiplication of cells, for example in order to utilize the excessive metabolizable energy.

In addition, it has been unexpectedly found according to the invention that the administration of whey permeate results in a prevention of the increase in β cell volume and that these substances result in a reduction of the volume of the pancreatic islets. The administration of the pharmaceutical compositions and preparations of this invention for these purposes is therefore preferred.

It has been preferred according to the invention that the use of whey permeate results in a lowering of the blood lipid values, particularly in a lowering of the triglyceride concentration.

It has further been surprisingly found that a treatment with whey permeate resulted in a partially significant lowering of the serum insulin level when applied alone or in combination with further effective substances. These effective substances are alpha glucosidase inhibitors, biguanides, glitazones, sulfonylureas, glinides, or insulin. The use of whey permeate as well as the use of preparations containing further active substances besides the whey permeate is also provided within the scope of this invention, as long as the further effective substances do not have a negative influence on the effect of the whey permeate.

In a further preferred embodiment, the whey permeate for the prevention or treatment of metabolic syndrome or type 2 diabetes is extracted from the milk of cattle, goats, sheep, buffalos, camels, or other milk-producing animals.

A particularly preferred embodiment is directed at the presence of the compositions or preparations of the invention containing whey permeate in the form of food supplements. Here also the use of (partially) hydrolyzed sweet whey permeate is preferred.

In a further preferred embodiment, whey permeate is used for producing dietary and/or enriched foodstuffs comprising suitable pharmaceutically acceptable additives. Examples of additives are colorants, flavor enhancers, preservatives, binding agents, or fillers known to those skilled in the art.

According to the invention, the above-mentioned substances may also be used for producing foodstuffs, for example dietary foodstuffs and/or food supplements, by which these become capable of preventing the metabolic syndrome or progression of type 2 diabetes and/or of relieving or curing the symptoms of these indications. Examples of such foodstuffs are dairy products or fruit juices enriched with compositions of the invention, however, other foodstuffs are also conceivable.

In the treatment and prevention of symptoms of metabolic syndrome and of type 2 diabetes with the help of whey permeate containing composition or preparations, the dosage is varied individually, where appropriate, according to disease indication, age, weight and gender of the person to be treated.

The concentration of the whey permeate containing compositions or preparations according to the invention in dietary and/or enriched foodstuffs may vary depending on the selected suitable additive and/or carrier, considering particularly the organoleptic properties of the final product.

Furthermore, compositions according to the invention may be contained in a combination preparation for prevention or treatment of symptoms of metabolic syndrome or type 2 diabetes. It is particularly preferred for a combination preparation to contain, in addition to the compositions of the invention, one or more of the following substances: alpha glucosidase inhibitors, biguanides, glitazones, glinides, and sulfonylureas. The administration of the combination preparations may also be adapted individually to the needs of the patient. According to the invention, these combination preparations may be administered separately in two or more separate doses, or together.

In addition, the use of a composition of the invention for producing a drug is particularly preferred, preferably for relieving or preventing the symptoms of metabolic syndrome and treating or preventing the development of type 2 diabetes, preventing the progression thereof as well as that of secondary diseases which may develop from the metabolic syndrome or diabetes.

The use of the combination preparations or drugs of the invention for the relief/prevention of the symptoms of the metabolic syndrome or type 2 diabetes is particularly directed at an application in humans, but the treatment of other mammals such as dogs, cats, horses, sheep, cows, or pigs, etc., is also included within the scope of protection.

The compositions and preparations of the invention are particularly preferred for the control/prevention of the growth of β cells in the pancreas, the multiplication of β cells in the pancreas, the increase in β-cell and/or islet volume, or pancreatitis in mammals, particularly humans.

Furthermore, it is particularly preferred for the use of the inventive compositions or preparations to result in a reduction of the serum insulin level.

It is further preferred that due to the administration of the compositions or preparations of the invention the development of glucose intolerance is prevented, or that the latter is mitigated.

In addition, it is preferred for the administration of the compositions or preparations of the invention to result in a delayed increase in morning hyperglycemia.

Furthermore, it is particularly preferred for the consumption of the compositions or preparations of the invention to result in a lowering of blood lipid values, particularly a lowering of the concentration of triglycerides, however, an influence on other blood lipids is also included in the scope of protection of the present invention.

According to the invention, calcium lactate is not added to the pharmaceutical compositions or preparations comprising whey permeate.

When there is an elevated content of trigylcerides in blood serum (>160 mg/100 ml), this is called hypertriglyceridemia (hyperlipemia). This condition may play a role in the development of arterial diseases and coronary heart disease (Vega and Grundy, Adv. Exp. Med. 243, 311 (1989)). In addition, severe hypertriglyceridemia (>1.000 mg/dl) is associated with chylomicronemia and causes acute pancreatitis (see K. Soergel, Acute Pancreatitis, in: Gastrointestinal Disease 91, $3^{rd}$ edition (Sleisenger, M. H. and Fordtran, J. S., eds.), W. B. Saunders Company, Philadelphia, Pa., 1983, p. 1462-1485; and Brown, M. S. and Goldstein, J. L., Drugs used in the Treatment of Hyperlipoproteinemias, in: Goodman and Gillman's, The Pharmacological Basis of Therapeutics 34, $7^{th}$ edition, (Macmillan Publishing Co., New York, 1985, p. 827-845). Serious increases in chylomicrons directly cause pancreatitis which could be prevented by reducing the triglycerides (U.S. Department of Health and Human Services, NIH-Publication No. 89-2925, p. 74-77, January 1989, "Report of the Expert Panel on Detection, Evaluation and Treatment of High Blood Cholesterol in Adults"). It has moreover been shown that the risk of a stroke in patients with coronary heart diseases may be lowered by reducing the content of triglycerides in plasma (D. Tanne, et al.; Circulation 2001, 104, 2892-2897). Furthermore, compared to non-diabetics, the life expectancy of type 2 diabetics is shortened by one third. This is probably directly associated with an elevated triglyceride level (Diabety Care; 2001, 24, 1335-1341). It is therefore desirable as part of the treatment of symptoms of metabolic syndrome or type 2 diabetes to also provide a procedure for reducing plasma triglycerides in patients with hypertriglyceridemia.

Oral administration of the inventive compositions or preparations is particularly preferred, however, other possibilities of administration are also included in the scope of protection according to the invention, e.g. parenteral, intravenous, etc.

In a particularly preferred embodiment, components of the compositions or preparations according to the invention are administered to prevent the symptoms of metabolic syndrome or type 2 diabetes, or in order to mitigate or cure these.

The concentration of whey permeate in a pharmaceutical or food supplement preparation lies between 0.01% and 99.99%, preferably between 0.1 and 99.9%, more preferably between 1 and 99%, particularly preferably between 1 and 80%, even more preferably between 10 and 80%, most preferably between 10 and 50%, relative to the total weight of the food supplement and/or the pharmaceutical preparation.

The food supplements according to the invention or the pharmaceutical preparations according to the invention may be taken or administered once or several times per day, e.g. in the morning, at noon, in the evening, together with, before or after meals, however, other administration plans are also conceivable.

The invention will now be explained with reference to experiments which are not intended to limit further the scope of the invention.

EXPERIMENTAL PART

Animal Models/Test Systems

Zucker rats were used as the animal model for studying the effect on limited glucose tolerance, disturbed lipid metabolism, on risk markers of cardiovascular changes and inflammation parameters.

The Zucker rat is the result of a spontaneous mutation in the 13M strain of Theodore and Lois Zucker in the Laboratory of Comparative Pathology in Stow, Mass. (phenotype fa=fatty), which led to the so-called "obese" or "fatty" phenotype. Both terms characterize rats that are overweight and obese.

The Zucker rat develops hyperphagia at an early stage, resulting in a rapid increase in body mass (overweight). At the age of 5 to 6 weeks, it has already developed hypertriglyceridemia, hyperlipemia, insulin resistance, accompanied by the development of glucose intolerance and hyperinsulinemia. At the age of 12 weeks, the glucose tolerance disorder becomes manifest, and hyperglycemia may develop and thus a manifestation of a clinical picture similar to type 2 diabetes. In this animal model, type 2 diabetes is accompanied by histopathological changes of the pancreatic islets. In addition, changes of the cardiovascular system were also reported in this animal model. Thus, an increase in blood pressure has been measured in 5- to 7-month-old animals (Yoshioka, Metabolism, Vol. 42 (1), 1993, p. 75 to 80).

The studies of the influence of whey permeate for controlling the metabolic syndrome were carried out on so-called WOK.W rats. The WOK.W rat is an animal model which transmits a polygenetic disorder and develops almost all symptoms of the metabolic syndrome, male animals expressing these symptoms in a more pronounced manner. The specific properties of WOK.W rats are described, for example, in:

P. Kovacs et al., *Ann. N.Y. Acad. Sci.*, 1997, 827, 94-99;
P. Kovacs et al., *Biochem. Biophsy. Res. Commun.*, 2000, 660-665;
J. van den Brandt et al., *Int. J. Obesity*, 2000, 24, 1618-1622;
J. van den Brandt et al., *Metabolism* 49, 2000, 1140-1144.

This model animal is suited to carry out exogenous modulation in the form of an intervention study when studying metabolic syndrome, especially since preliminary studies show that the disease incidence may be changed, for example, by fat-rich nutrition.

Animal Maintenance:

The animals were kept under semi-barrier conditions with a 12:12 hr light/dark cycle (light from 6:00 a.m. to 6:00 p.m.). Access to food (RM standard diet, Sniff, Soest, Germany) and drinking water was permanently possible for them.

TABLE 1

Administered amount of the respective substances:

| Test substance | Dose | Application |
|---|---|---|
| Sweet whey permeate (SMP) | 25 g/l; corresponding to approx: 1.5 g/kg/day | dissolved in acidified drinking water |
| Control | | acidified drinking water |

Application of the Substances

The substances were dissolved in acidified drinking water (25 g/l) and offered ad libitum to the animals instead of acidified drinking water without supplement. The control group received pure acidified drinking water (pH 2.65) (in experimental animal maintenance, tap water is acidified with hydrochloric acid to reduce germs). The amount drunk was monitored daily, and the drinking water was always freshly prepared.

Analytical Methods

The concentration of blood glucose and lactate was measured by means of *Glucoseanalyzer* (Super GL Ambulance, Ruhrtal Labortechnik, Germany).

The determination of the concentration of immuno-reactive insulin (IRI) was effected by means of rat insulin-specific radioimmunoassay (Linco Research, Inc.; USA).

The determination of total cholesterol, HDL cholesterol, LDL cholesterol, and triglycerides occurred photometrically.

C-reactive protein was determined turbidimetrically.

The determination of the number of leucocytes occurred by means of the counting chamber method.

Evaluation Methods:

Display of blood glucose and insulin curves in the oral glucose tolerance test oGTT starting from the point in time −10 min before glucose administration up to 120 min thereafter. The mean curves for the test groups were represented for each parameter for the respective time of treatment. In order to judge the physiological and the treatment effects, the reactive and absolute excess areas were calculated for individual parameters corresponding to the study protocol for blood glucose and insulin (G-AUC and I-AUC from 0-120 min: FIGS. 4(a) and (b), 5(a) and (b), 6(a) and (b)).

For this, the data regarding blood glucose and insulin concentrations were documented depending on the time of sampling. The reactive area was calculated as follows:

absolute area (absolute AUC, area under curve) Fa=area under the curve of the concentration of blood glucose or insulin, depending on time (0-120 min)

reactive area (reactive AUC): $Fr = Fa - t \cdot y_0$ (t=total duration of the experiment, $y_0$=basal concentration of blood glucose or insulin)

Explanation of the calculation, using the blood glucose concentration as an example:

With a total duration of the experiment of 120 min and the sampling times −10, 0, 10, 20, 30, 40, 60, 90, 120 stipulated in the experimental design, the absolute areas from 0 to 120 min are calculated as follows:

$$Fa = (10 y_0 + 20 y_{10} + 20 y_{20} + 20 y_{30} + 30 y_{40} + 50 y_{60} + 60 y_{90} + 30 y_{120})/2$$

$$F_r = F_a - 120 y_0$$

Measuring units: G-AUC in mmol×min/l
I-AUC in ng×min/ml

Pairwise comparison: The difference was formed between test and control situation, and it was tested using the t-test whether this difference was different from 0 (p<0.05).

Comparison of mean values using t-test.

Exceptional anomaly test according to "*Verfahrensbibliothek: Versuchsplanung und-auswertung*", Volume 1, Berlin 1978, Rasch D. et al., p. 408.

Procedure/Experimental Design:

The Zucker rats were moved into hutches at the age of about 14 weeks, and the tests were initiated after one week of adaptation. At the age of 15 weeks, the animals were initially characterized with respect to parameters regarding glucose and lipid metabolism (inter alia blood glucose, concentration of serum insulin, cholesterol and triglycerides), glucose tolerance (by means of oral glucose tolerance test) as well as inflammation markers (number of leucocytes and C-reactive protein). The blood samples necessary for this were taken from the tail vein. Then, the treatment was initiated. The determination of blood glucose concentration, body mass, number of leucocytes, and feed intake was effected continuously in weekly intervals. The intake of drinking water was monitored daily. After 2 and 6 weeks of treatment, parameters of glucose and lipid metabolism were newly measured and the glucose tolerance was determined.

In order to determine the glucose tolerance, glucose tolerance tests were carried out after food deprivation during the night. During this, blood samples were taken in the period from 10 min before glucose application (via gastric tube) to 120 min after glucose administration (2 g/kg) in order to determine blood glucose (sampling times: −10, 0, 10, 20, 30, 40, 60, 90, and 120 min) and insulin concentration (sampling times: 0, 20, 40, 60, 90, and 120 min). Before initiation of the treatment and 6 weeks thereafter, a daily profile (3 hr interval) of blood glucose and lactose concentration was produced. After termination of the regular 43-day observation period, the treatment regime was also maintained after carrying out the final oral glucose tolerance tests until processing on the $62^{nd}/63^{rd}$ day of treatment. The animals were killed by means of anesthetic overdose. After anesthesia had occurred, the pancreases were removed, and then fixed and stored for subsequent histological study in Bouin's solution.

Sample Storage:

All serum samples were stored in the freezer at −20° C. until analysed.

Results:

Follow-Up Studies:

Intake of Feed and Drinking Water

Although the amount drunk was slightly increased in animals treated with SMP (FIG. 1), the amount of calories consumed daily was comparable in all groups (FIG. 1a). The groups do not differ to a significant extent as regards their daily feed intake (FIG. 1). The calculated energy intake on the $42^{nd}$ treatment day was:

SMP group: 87.6±6.6 kcal/24 hr

Control: 87.9±25.5 kcal/24 hr

Differences between the groups could not be validated.

Development of Body Mass

The treatment groups do not differ as regards the development of their body mass (FIG. 2).

Blood Glucose and Insulin Curve

Before start of treatment, i.e. at the age of 15 weeks, the concentration of blood glucose (FIG. 2) and the concentration of insulin (FIG. 3a) of the animals in the study groups were comparable. While in the control group after initiation of treatment the morning blood glucose continued to rise, as expected in this animal model during the course of ageing, this rise remained largely inexistent in the SMP group.

Compared to the time before initiation of treatment (n.s./not significant), the insulin concentration (FIG. 3a) in the group treated with SMP dropped as the duration of the treatment increased. The insulin concentrations remained at an unchanged level (control).

Lipid Metabolism Parameters

The concentrations of non-esterified fatty acids remained unchanged during the period of observation. There were no differences between the treatment groups (FIG. 3a).

Compared to the control group, the cholesterol concentrations increased during the period of observation, as opposed to the SMP group (n.s., FIG. 3b).

The concentrations of HDL cholesterol remained unchanged during the period of observation (FIG. 3b). Only before initiation of treatment were there differences between the groups, which were, however, insignificant for the effect of the treatment.

While the rise in LDL cholesterol concentration (FIG. 3c), as could be observed in the control group, could not be prevented by SMP treatment, it proved to be less than in the control group (n. s.).

A tendency for lowering the triglyceride concentration was recognizable in the group of animals treated with SMP (FIG. 3c).

Inflammation Parameters

The inflammation parameters C-reactive protein (FIG. 3d) and number of leucocytes did not alter during the therapies in the period of observation.

Results of the Oral Glucose Tolerance Tests:

The curves of blood glucose and insulin concentrations during the oral glucose tolerance test (oGTT) of the groups before treatment were comparable (FIGS. 4a and 4b).

After 3 weeks of treatment, no significant differences between the treatment groups regarding curve and excess areas of blood glucose and insulin were detectable (FIGS. 5a and b).

After 6 weeks of treatment, blood glucose in the GTT of the SMP group increased considerably less and after a 120 min period of observation it dropped to a significantly lower level compared to the control group (FIGS. 6a and b).

Analysis of the blood glucose curves (BG, mmol/l) of the GTTs before and after 6 weeks of therapy, mean±SD (* $p < 0.05$ vs. control):

TABLE 2

| Group | Parameter | Before treatment | After 6 weeks |
|---|---|---|---|
| SMP | BG −10 min | 4.94 ± 0.69 | 5.29 ± 0.79 |
|  | BG max | 11.64 ± 0.75 | 12.61 ± 2.10 |
|  | BG 120 min | 7.95 ± 1.27 | 8.02 ± 1.42* |
| Control | BG −10 min | 4.84 ± 1.17 | 5.62 ± 0.59 |
|  | BG max | 11.99 ± 2.03 | 14.25 ± 1.58 |
|  | BG 120 min | 8.08 ± 2.14 | 10.22 ± 2.19 |

After 6 weeks of treatment, the glucose tolerance, measured as glucose excess area (G-AUC) in the GTT, had improved significantly in the group treated with SMP compared to the control group. While G-AUC in the control group increased during the period of observation, it was comparable to that before initiation of treatment in the group treated with SMP.

Evaluation of the reactive G-AUC 0-120 min (mmol× min/l) before and after 6 weeks of treatment, mean±SD ($p < 0.05$ vs. control):

TABLE 3

| Group | Before treatment | After 6 weeks |
|---|---|---|
| SMP | 570 ± 75 | 569 ± 145 |
| Control | 597 ± 124 | 780 ± 138 |

TABLE 4

Comparison of selected parameters of patients and WOK.W rats

| Parameter | WOK.W rat | HUMAN |
|---|---|---|
| Obesity | +++[1] | +++ |
| Hypertriglyceridemia | +++ | +++ |
| Hypercholesterolemia | + | ++[2] |
| Dyslipoproteinemia | ++ | +++ |
| Reduced HDL cholesterol | +[3] | ++ |
| Hyperleptinemia | +++ | +++ |
| Glucose intolerance | ++ | +++ |
| Insulin resistance | ++ | +++ |
| Hyperinsulinemia | ++ | ++ |
| Hypertension | + | +++ |

[1] +++ = very strongly pronounced,
[2] ++ = strongly pronounced,
[3] + = present The above table clarifies why the WOK.W rat is a highly suitable animal model for metabolic syndrome in humans.

Pancreas Morphometry

The examined pancreases were removed at the age of 16 weeks, i.e. after a 12-week treatment period. The pancreases were embedded in paraffine and cut with a slice thickness of 7 μm. Every tenth slice was either stained with Hematoxilin-eosin (to show the volume of the islets and to evaluate inflammation) or incubated with anti-insulin antibodies (to show the β cell volume). In order to evaluate inflammation (insulitis), 15 islets were counted. The immunohistochemical reaction was visualized with APAAP (stained in red). The morphometric evaluation of the distribution of the islet cells and the insulin-forming β cells compared to exocrine cells, fibrous tissue and vessels was effected by counting 40,000 points of a net lying on top of the preparation. Four animals of each group were used in each case.

TABLE 5

Results of the immunohistochemical examination of the pancreases

|  | Islet volume | β cell volume | Non β cell volume |
|---|---|---|---|
| Control (n = 8) | 1.12 ± 0.06 (1.00-1.53) | 0.98 ± 0.02 (0.86-1.06) | 0.14 ± 0.05 (0.02-0.47) |
| SMP (n = 7) | 0.79 ± 0.12 (0.41-1.21) | 0.63 ± .010 (0.27-0.86) | 0.17 ± 0.04 0.00-0.36 |
| P (vs. control) | <0.01 | <0.005 | not significant |

The pancreas morphometry of the WOK.W rats showed that a morphological correlate for hyperinsulinism could be found (see table 5 above). This manifested itself in an increase in the β cell volume, the appearance of small clusters of β cells in the exocrine pancreas, the detection of β cells in the epithelia of the pancreas duct (indication of neogenesis) and an increase in the β cell mitosis number, which are causally involved in the development of hyperinsulinism. The detected morphology suggests an increased demand on this organ (e.g. by the increase in metabolizable energy), which was compensated in part by cell multiplication.

By application of whey permeate in the drinking water, the increase in β cell volume is prevented or significantly reduced after a 12-week period of treatment.

Although whey is highly energetic, the appearance of selective inflammation of the islets and/or β cells (insulitis) was not detectable in any of the examined animals.

Study of Serum Insulin Levels in WOK.W Rats

The study of the serum insulin levels in treated rats showed that they exhibited no increase or a lower increase in the serum insulin level during the period of treatment when compared with control rats.

TABLE 6

Serum insulin values (ng/ml) of treated and untreated WOK.W rats compared to controls of identical age.

| Group | 8 weeks | 16 weeks | p |
|---|---|---|---|
| Control | 3.61 ± 0.24 | 6.12 ± 0.61 | <0.01 |
| SMP | 3.77 ± 0.36 | 4.47 ± 0.64 | not significant |

During the observation period, the increase in glucose intolerance is prevented by treatment with SMP.

Insulin release during the oral glucose tolerance test (measured as insulin excess area; I-AUC) was highest after 6 weeks of treatment in the group of animals treated with SMP.

Insulin release in the oGTT was best stimulated after 6 weeks of SMP treatment. However, the released insulin led only in the SMP group to a significant reduction in blood glucose in the oGTT.

TABLE 7

Assay of reactive I-AUC 0-120 min (ng × min/l), mean ± SD (standard deviation):

| Group | Before treatment | After 6 weeks |
|---|---|---|
| SMP | 578 ± 667 | 897 ± 120 |
| Control | 711 ± 664 | 745 ± 506 |

After 6 weeks of treatment, the β cells of the pancreas of the animals from the SMP group were best capable of reacting to the glucose stimulus. In addition, the animals were less insulin-resistant.

Diurnal Profiles of Blood Glucose and Lactate:

At the times before and after 6 weeks of treatment, the diurnal profiles of blood glucose show no significant differences between the treatment groups (FIGS. 7 and 8), the blood glucose concentrations of the group treated for 6 weeks with SMP being, however, lowest in the course of the day.

At some times, the diurnal profile of lactate shows significant differences between the groups. Lactic acidosis could, however, be excluded at any time (FIGS. 7 and 8). The higher lactate concentrations before initiation of treatment are interpreted as stress reactions, since a familiarization effect of the animals to the blood sampling can still not have occurred at this time.

The invention claimed is:

1. A method for the treatment of metabolic syndrome or type 2 diabetes in a mammal comprising administering a composition comprising whey permeate to a mammal in need thereof.

2. The method according to claim 1, wherein symptoms of metabolic syndrome or type 2 diabetes are selected from glucose intolerance and insulin resistance.

3. The method according to claim 1, wherein the whey permeate is sweet whey permeate.

4. The method according to claim 1, wherein the whey permeate is reduced in lactose.

5. The method according to claim 1, wherein the composition is microencapsulated.

6. The method according to claim 1, herein the composition is formed as an oral form of administration.

7. The method according to claim 6, wherein the oral form of administration is a lozenge, a powder, granules, a syrup or a juice.

8. The method according to claim 1, wherein the composition is a food supplement.

9. The method according to claim 8, wherein the composition is a dietary foodstuff.

10. The method according to claim 1, wherein the composition further comprises pharmaceutically acceptable additives and/or carriers.

11. The method according to claim 1, Wherein the mammal is a human.

12. The method according to claim 1, wherein the whey permeate is hydrolyzed.

13. The method according to claim 1, wherein the whey permeate is partially hydrolyzed.

14. The method according to claim 1 wherein the concentration of whey permeate present in the composition is between 0.01% and 99.99% by weight.

15. The method according to claim 1 wherein the concentration of whey permeate present in the composition is between 0.1% and 99.9% by weight.

16. The method according to claim 15 wherein the concentration of whey permeate present in the composition is between 1 and 99% by weight.

17. The method according to claim 16 wherein the concentration of whey permeate present in the composition is between 1 and 80% by weight.

18. The method according to claim 17 wherein the concentration of whey permeate present in the composition is between 10 and 80% by weight.

19. The method according to claim 18 Wherein the concentration of whey permeate present in the composition is between 10 and 50% by weight.

* * * * *